(12) United States Patent
Abdur-Rashid et al.

(10) Patent No.: US 11,008,270 B2
(45) Date of Patent: May 18, 2021

(54) CATALYTIC CONVERSION OF CARBON DIOXIDE TO METHANOL USING DIFORMATE ESTERS AS INTERMEDIATES

(71) Applicant: Kare Chemical Technologies Inc., Milton (CA)

(72) Inventors: Kareem Abdur-Rashid, Mississauga (CA); Wenli Jia, Toronto (CA); Kamaluddin Abdur-Rashid, Mississauga (CA)

(73) Assignee: Kare Chemical Technologies Inc., Milton (CA)

( * ) Notice: Subject to any disclaimer, the term of this patent is extended or adjusted under 35 U.S.C. 154(b) by 0 days.

(21) Appl. No.: 17/044,579

(22) PCT Filed: Apr. 1, 2019

(86) PCT No.: PCT/IB2019/052669
§ 371 (c)(1),
(2) Date: Oct. 1, 2020

(87) PCT Pub. No.: WO2019/193483
PCT Pub. Date: Oct. 10, 2019

(65) Prior Publication Data
US 2021/0087126 A1    Mar. 25, 2021

Related U.S. Application Data (60) Provisional application No. 62/653,896, filed on Apr. 6, 2018.

(51) Int. Cl.
| | | |
|---|---|---|
| *C07C 29/151* | (2006.01) |
| *C07C 29/153* | (2006.01) |
| *C07C 29/154* | (2006.01) |
| *C07C 29/156* | (2006.01) |

(Continued)

(52) U.S. Cl.
CPC .......... *C07C 29/153* (2013.01); *C07C 29/136* (2013.01); *C07C 29/151* (2013.01);
(Continued)

(58) Field of Classification Search
None
See application file for complete search history.

(56) References Cited

U.S. PATENT DOCUMENTS

| | | |
|---|---|---|
| 7,291,753 B2 | 11/2007 | Abdur-Rashid |
| 7,317,131 B2 | 1/2008 | Rautenstrauch et al. |

(Continued)

FOREIGN PATENT DOCUMENTS

| | | |
|---|---|---|
| CA | 2636946 | 7/2007 |
| CA | 2642387 | 8/2007 |
| CA | 2636947 | 1/2009 |

OTHER PUBLICATIONS

C.A. Huff et al., Cascade Catalysis for the Homogeneous Hydrogenation of CO2 to Methanol. J. Am. Chem. Soc. 2011, 133, 18122-18125.

(Continued)

*Primary Examiner* — Medhanit W Bahta
(74) *Attorney, Agent, or Firm* — Bereskin & Parr LLP/S.E.N.C.R.L., s.r.l.; Michael Fenwick (57) ABSTRACT

The present disclosure relates to a new catalytic process for the production of methanol from carbon dioxide, comprising: (1) the conversion of carbon dioxide and hydrogen to formic acid or formate salts; (2) converting the formic acid or formate salts to diformate esters of diols; (3) hydrogenating the diformate esters to methanol and diols. The diols produced from the hydrogenation reaction can be recovered and re-used to prepare the diformate esters.

14 Claims, 5 Drawing Sheets

(51) Int. Cl.
    C07C 29/157    (2006.01)
    C07C 29/158    (2006.01)
    C07C 29/136    (2006.01)
(52) U.S. Cl.
    CPC .......... C07C 29/154 (2013.01); C07C 29/156 (2013.01); C07C 29/157 (2013.01); C07C 29/158 (2013.01); C07C 2531/16 (2013.01)

(56) References Cited

U.S. PATENT DOCUMENTS

| | | | |
|---|---|---|---|
| 7,579,295 | B2 | 8/2009 | Rautenstrauch et al. |
| 7,772,445 | B2 | 8/2010 | Chen et al. |
| 7,777,083 | B2 | 8/2010 | Abdur-Rashid et al. |
| 8,232,430 | B2 | 7/2012 | Abdur-Rashid et al. |
| 8,518,368 | B2 | 8/2013 | Abdur-Rashid et al. |
| 8,658,825 | B2 | 2/2014 | Abdur-Rashid et al. |
| 8,716,508 | B2 | 5/2014 | Abdur-Rashid et al. |
| 9,115,249 | B2 | 8/2015 | Abdur-Rashid et al. |
| 9,216,933 | B2 | 12/2015 | Klankermayer et al. |

OTHER PUBLICATIONS

S. Wesselbaum et al., Hydrogenation of Carbon Dioxide to Methanol by Using a Homogeneous Ruthenium—Phosphine Catalyst. Angew. Chem. Int. Ed. 2012, 51, 7499-7502.

E. Balaraman et al., Efficient Hydrogenation of Organic Carbonates, Carbamates and Formates Indicates Alternative Routes to Methanol Based on CO2 and CO. Nature Chemistry 2011, 3, 609-614.

Z. Han et al., Catalytic Hydrogenation of Cyclic Carbonates: A Practical Approach from CO2 and Epoxides to Methanol and Diols. Angew. Chem. Int. Ed. 2012, 51, 13041-13045.

K. Abdur-Rashid et al.,Synthesis of Ruthenium Hydride Complexes Containing beta-Aminophosphine Ligands Derived from Amino Acids and their use in the H2-Hydrogenation of Ketones and Imines. Adv. Synth. Catal. 2005, 347, 571-579.

D. Amoroso et al.,Improved Catalysts and Ligands for Asymmetric Synthesis. Aldrichimica Acta 2008, 41, 15-26.

W. Jia et al., Aminophosphine ligands R2P(CH2)nNH2 and ruthenium hydrogenation catalysts RuCl2(R2P(CH2)nNH2) 2. Dalton Trans. 2009, 8301-8307.

R. Guo et al., Synthesis of Chiral Aminophosphines from Chiral Aminoalcohols via Cyclic Sulfamidates. J. Org. Chem. 2010, 75, 937-940.

C.-W. Tsang et al.,Quaternized aminophosphines a stable and convenient entry to valuable catalysts. Chimica Oggi 2010, 28, 18-22.

Clarke et al., A Family of Active Iridium Catalysts for Transfer Hydrogenation of Ketones. Organometallics, 2006, 25, 4113-4117.

X. Chen et al., Highly active iridium catalysts for the hydrogenation of ketones and aldehydes. Dalton Trans. 2009, 1407-1410.

T.W. Graham et al., Catalytic Solvolysis of Ammonia Borane. Angew. Chem. Int. Ed. 2010, 49, 8708-8711.

D. Amoroso et al., Aminodiposphines: Highly Versatile Ligands for Catalysis.The Strem Chemiker 2011, 25, 4-12.

CATALYTIC CONVERSION OF CARBON DIOXIDE TO METHANOL USING DIFORMATE ESTERS AS INTERMEDIATES

CROSS-REFERENCE TO RELATED APPLICATIONS

The present application is a national phase entry of PCT/IB2019/052669 filed Apr. 1, 2019, which claims the benefit of priority of U.S. Provisional Patent Application No. 62/653,896 filed on Apr. 6, 2018, the contents of which are incorporated herein by reference in their entirety.

FIELD OF THE DISCLOSURE

The present disclosure relates to catalytic hydrogenation of diformate esters to methanol and diols. The diformate esters are derived from formic acid or formate salts, which in turn are derived from carbon dioxide and hydrogen. The diols produced from the hydrogenation reaction can be recovered and re-used to prepare the diformate esters. The disclosure is a catalytic process for the conversion of carbon dioxide to methanol.

BACKGROUND OF THE DISCLOSURE

Carbon dioxide is a cheap, safe and renewable source of carbon. However, carbon dioxide is also a greenhouse gas and is of significant environmental concern. Catalytic hydrogenation of carbon dioxide to methanol is regarded as a significant component of a methanol economy, as it is a liquid hydrocarbon that can be easily stored and transported (G. A. Olah et al., *Beyond Oil and Gas. The Methanol Economy*, Wiley-VCH, 2006). Methanol is valuable industrially, both as a fuel and a chemical feedstock. The direct conversion of carbon dioxide and hydrogen to methanol, using heterogeneous and homogeneous catalysts, has been explored by several groups (C. A. Huff et al., *J. Am. Chem. Soc.* 2011, 133, 18122-18125; S. Wesselbaum et al., *Angew. Chem. Int. Ed.* 2012, 51, 7499-7502). However, such procedures are generally expensive and inefficient, and require high temperatures and pressures.

Over the years, several catalytic processes have been developed to produce methanol from a variety of precursors. Milstein and coworkers (E. Balaraman et al., *Nature Chemistry* 2011, 3, 609-614) reported the use of homogeneous catalysts for the hydrogenation of methyl formate and dimethyl carbonate to methanol. The drawback for this process is that the dimethyl carbonate is derived from, and is more expensive that methanol.

Ding et al. (Z. Han et al., *Angew. Chem. Int. Ed.* 2012, 51, 13041-13045) reported the hydrogenation of carbonate esters to diols and methanol. However, the carbonate esters are derived from alkene oxides, which are more expensive than methanol, and the diol by-product cannot be readily converted to carbonate esters or alkene oxides.

Hence, there is still a need for an effective and efficient catalytic process to directly or indirectly convert carbon dioxide and hydrogen to methanol. Abdur-Rashid et al. reported the use of ruthenium aminophosphine (PN) catalysts (U.S. Pat. Nos. 7,317,131; 7,579,295; 7,772,445; 8,232,430; 8,658,825; 8,716,508; 9,115,249; K. Abdur-Rashid et al., *Adv. Synth. Catal.* 2005, 347, 571-579; D. Amoroso et al., *Aldrichimica Acta* 2008, 41, 15-26; W. Jia et al., *Dalton Trans.* 2009, 8301-8307; R. Guo et al., *J. Org. Chem.* 2010, 75, 937-940; C.-W. Tsang et al., *Chimica Oggi* 2010, 28, 18-22) as well as metal aminodiphosphine (PNP) catalysts (U.S. Pat. Nos. 7,291,753; 7,777,083; 8,518,368; Z. Clarke et al., *Organometallics*, 2006, 25, 4113-4117; X. Chen et al., *Dalton Trans.* 2009, 1407-1410; T. W. Graham et al., *Angew. Chem. Int. Ed.* 2010, 49, 8708-8711; D. Amoroso et al., *The Strem Chemiker* 2011, 25, 4-12) for the hydrogenation and transfer hydrogenation of carbonyl (C=O), and iminocarbonyl (C=N) and alkene (C=C) bonds. These reports and those of other researchers have demonstrated the applications of these and related catalysts for the broad scope reduction of a variety of carbonyl compounds, including ketones, aldehydes, esters, amides and carbonate esters.

SUMMARY OF THE DISCLOSURE

This disclosure provides a method for the catalytic preparation of methanol by the hydrogenation of diformate esters. Such diformate esters are readily derived from the reaction of formic acid and diols, or from formate salts and diols. The formic acid and formate salts are derived from the catalytic reaction between carbon dioxide and hydrogen.

The hydrogenation of the diformate esters produces methanol and diols. Such diols can be readily separated from the methanol by distillation. The recovered diols can be readily converted back to diformate esters. Hence, the disclosure provides a method by which a non-volatile and recoverable by-product can be repeatedly recycled and re-used for the conversion of carbon dioxide to methanol. In addition, simple diols such as ethylene glycol, propylene glycol and diethylene glycol can be derived from sustainable and renewable sources, such as glycerol and ethanol.

Accordingly, the present disclosure relates to the catalytic hydrogenation of a diformate ester of the Formula (I):

wherein, Y represents an unsubstituted or substituted alkylene, or an unsubstituted or substituted alkenylene, or an unsubstituted or substituted arylene, where adjacent or geminal substituents on Y may be joined together to form, including the atoms to which they are attached, one or more unsubstituted or substituted monocyclic, polycyclic, heterocyclic, carbocyclic, saturated, unsaturated or metallocenyl ring systems, and/or one or more of the carbon atoms in Y is optionally replaced with a heteromoiety selected from O, S, NH and N($C_{1-6}$alkyl) and Y is chiral or achiral.

The present disclosure relates to the catalytic hydrogenation of a diformate ester of the Formula (I) to form methanol and a diol of the Formula (II):

wherein, Y represents an unsubstituted or substituted alkylene, or an unsubstituted or substituted alkenylene, or an unsubstituted or substituted arylene, where adjacent or geminal substituents on Y may be joined together to form, including the atoms to which they are attached, one or more unsubstituted or substituted monocyclic, polycyclic, heterocyclic, carbocyclic, saturated, unsaturated or metallocenyl ring systems, and/or one or more of the carbon atoms in Y is optionally replaced with a heteromoiety selected from O, S, NH and N($C_{1-6}$alkyl) and Y is chiral or achiral.

In the present disclosure, it has been shown that a variety of ligands and metals may be used to catalyze the hydrogenation of the diformate esters to methanol and diols. In an embodiment of the disclosure, the metal includes chromium (Cr), manganese (Mn), iron (Fe), cobalt (Co), nickel (Ni), copper (Cu), molybdenum (Mo), ruthenium (Ru), rhodium (Rh), palladium (Pd), tungsten (W), rhenium (Re), osmium (Os), iridium (Ir) and platinum (Pt). In embodiments of the disclosure, the metal is a transition metal. In other embodiments of the disclosure, the metal is selected from Mn, Fe, Ru, Os, Co, Rh, Re and Ir.

With respect to the identity of the ligands, the metal catalyst comprises at least one ligand that bonds to the metal via a nitrogen atom. The nitrogen must have a pair of electrons available for binding but may be saturated (primary, secondary or tertiary amine) or unsaturated (imine or aromatic amine). There are many such ligands known in the art. In an embodiment of the disclosure, the nitrogen-coordinating ligand is selected from one or more of a PN, PNP, PNNP or PNN ligand wherein, PN is a bidentate ligand of the formula $R_1R_2P-Q^1-NR^1R^2$;
PNP is a tridentate ligand of the formula $R_3R_4P-Q^2-NR^3-Q^3-PR_5R_6$;
PNNP is a tetradentate ligand of the formula $R_7R_8P-Q^4-NR^4-Q^5-NR^5-Q^6-PR_9R_{10}$;
PNN is a tridentate ligand of the formula $R_{11}R_{12}P-Q^7-NR^6-Q^8-NR^7R^8$;
Wherein
$R_1$-$R_{12}$ are independently selected from unsubstituted or substituted $C_{1-10}$alkyl, unsubstituted or substituted $C_{2-10}$alkenyl, unsubstituted or substituted $C_{3-10}$cycloalkyl, unsubstituted or substituted $C_{6-14}$aryl, or any two adjacent or geminal $R_1$-$R_{12}$ groups are bonded together to form, together with the atoms to which they are attached, a 5-14-membered monocyclic, polycyclic, heterocyclic, carbocyclic, saturated or unsaturated ring system and any of $R_1$-$R_{12}$, including rings formed therewith are achiral or chiral; and
$R^1$-$R^8$ are independently selected from H, $C_{1-10}$alkyl, or aryl; and
$Q^1$-$Q^8$ are independently selected from unsubstituted or substituted $C_1$-$C_{10}$alkylene and unsubstituted or substituted $C_1$-$C_{10}$alkenylene where adjacent or geminal substituents on $Q^1$-$Q^8$ are joined together to form, including the atoms to which they are attached, one or more unsubstituted or substituted 5-14-membered monocyclic, polycyclic, heterocyclic, carbocyclic, saturated, unsaturated or metallocenyl ring systems, and/or one or more of the carbon atoms in $Q^1$-$Q^8$ is optionally replaced with a heteromoiety selected from O, S, NH and N($C_{1-6}$alkyl) and any of $Q^1$-$Q^8$ is chiral or achiral.

The metal catalysts may also comprise one or more of non-coordinating or coordinating, neutral or anionic and/or Lewis basic ligands, depending on the valency and size characteristics of the metal as would be known to those skilled in the art. Examples of such ligands include, but are not limited to phosphines, diphospines, cyclooctene, cyclooctadiene, halo (in particular Cl), OH, H, CO, pyridine, benzene, benzene derivatives and acetonitrile. The catalyst may also be neutral, monocationic or dicationic.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

The invention will be described in greater detail with reference to the following drawings in which.

DETAILED DESCRIPTION OF THE DISCLOSURE (I) Definitions

The term "alkyl" as used herein means straight and/or branched chain, saturated alkyl radicals containing one or more carbon atoms and includes (depending on the identity) methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like.

The term "alkenyl" as used herein means straight and/or branched chain, unsaturated alkyl radicals containing two or more carbon atoms and one to three double bonds, and includes (depending on the identity) vinyl, allyl, 2-methyl-prop-1-enyl, but-1-enyl, but-2-enyl, but-3-enyl, 2-methyl-but-1-enyl, 2-methylpent-1-enyl, 4-methylpent-1-enyl, 4-methylpent-2-enyl, 2-methylpent-2-enyl, 4-methylpenta-1,3-dienyl, hexen-1-yl and the like.

The term "alkynyl" as used herein means straight and/or branched chain, unsaturated alkyl radicals containing two or more carbon atoms and one to three triple bonds, and includes (depending on the identity) acetylynyl, propynyl, but-1-ynyl, but-2-ynyl, but-3-ynyl, 3-methylbut-1-enyl, 3-methylpent-1-ynyl, 4-methylpent-1-ynyl, 4-methylpent-2-ynyl, penta-1,3-di-ynyl, hexyn-1-yl and the like.

The term "alkoxy" as used herein means straight and/or branched chain alkoxy group containing one or more carbon atoms and includes (depending on the identity) methoxy, ethoxy, propyloxy, isopropyloxy, t-butoxy, heptoxy, and the like.

The term "cycloalkyl" as used herein means a monocyclic, bicyclic or tricyclic saturated carbocylic group containing three or more carbon atoms and includes (depending on the identity) cyclopropyl, cyclobutyl, cyclopentyl, cyclodecyl and the like.

The term "aryl" as used herein means a monocyclic, bicyclic or tricyclic aromatic ring system containing at least one aromatic ring and 6 or more carbon atoms and includes phenyl, naphthyl, anthracenyl, 1,2-dihydronaphthyl, 1,2,3,4-tetrahydronaphthyl, fluorenyl, indanyl, indenyl and the like.

The term "heteroaryl" as used herein means a monocyclic, bicyclic or tricyclic ring system containing one or two aromatic rings and 5 or more atoms of which, unless otherwise specified, one, two, three, four or five are heteromoieties independently selected from N, NH, N(alkyl), O and S and includes thienyl, furyl, pyrrolyl, pyrididyl, indolyl, quinolyl, isoquinolyl, tetrahydroquinolyl, benzofuryl, benzothienyl and the like.

The term "halo" as used herein means halogen and includes chloro, fluoro, bromo or iodo.

The term "fluoro-substituted" as used herein means that at least one, including all, of the hydrogens on the referenced group is replaced with fluorine.

The suffix "ene" added on to any of the above groups means that the group is divalent, i.e. inserted between two other groups.

The term "ring system" as used herein refers to a carbon-containing ring system, that includes monocycles, fused bicyclic and polycyclic rings, bridged rings and metalocenes. Where specified, the carbons in the rings may be substituted or replaced with heteroatoms.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

(II) Processes of the Disclosure

In an embodiment of the invention, there is hydrogenation of diformate esters of Formula (I):

(I)

wherein, Y represents an unsubstituted or substituted alkylene, or an unsubstituted or substituted alkenylene, or an unsubstituted or substituted arylene, where adjacent or geminal substituents on Y may be joined together to form, including the atoms to which they are attached, one or more unsubstituted or substituted monocyclic, polycyclic, heterocyclic, carbocyclic, saturated, unsaturated or metallocenyl ring systems, and/or one or more of the carbon atoms in Y is optionally replaced with a heteromoiety selected from O, S, NH and N($C_{1-6}$alkyl) and Y is chiral or achiral, to provide the corresponding hydrogenated compounds of Formula (II) and methanol (Formula (III)):

(II)

(III)

wherein, Y represents an unsubstituted or substituted alkylene, or an unsubstituted or substituted alkenylene, or an unsubstituted or substituted arylene, where adjacent or geminal substituents on Y may be joined together to form, including the atoms to which they are attached, one or more unsubstituted or substituted monocyclic, polycyclic, heterocyclic, carbocyclic, saturated, unsaturated or metallocenyl ring systems, and/or one or more of the carbon atoms in Y is optionally replaced with a heteromoiety selected from O, S, NH and N($C_{1-6}$alkyl) and Y is chiral or achiral.

In an embodiment of the invention, it has been shown that a variety of ligands and metals may be used to catalyze the hydrogenation of the diformate esters to methanol and diols. In an embodiment of the disclosure, the metal includes chromium (Cr), manganese (Mn), iron (Fe), cobalt (Co), nickel (Ni), copper (Cu), molybdenum (Mo), ruthenium (Ru), rhodium (Rh), palladium (Pd), tungsten (W), rhenium (Re), osmium (Os), iridium (Ir) and platinum (Pt). In embodiments of the disclosure, the metal is a transition metal. In other embodiments of the disclosure, the metal is selected from Mn, Fe, Ru, Os, Co, Rh, Re and Ir.

In another embodiment of the invention, the metal catalyst comprises at least one ligand that bonds to the metal via a nitrogen atom. In an embodiment of the disclosure, the nitrogen-coordinating ligand is selected from one or more of PN, PNP, PNNP or PNN ligand wherein, PN is a bidentate ligand of the formula $R_1R_2P-Q^1-NR^1R^2$;
PNP is a tridentate ligand of the formula $R_3R_4P-Q^2-NR^3-Q^3-PR_5R_6$;
PNNP is a tetradentate ligand of the formula $R_7R_8P-Q^4-NR^4-Q^5-NR^5-Q^6-PR_9R_{10}$;
PNN is a tridentate ligand of the formula $R_{11}R_{12}P-Q^7-NR^6-Q^8-NR^7R^8$;
Wherein
$R_1$-$R_{12}$ are independently selected from unsubstituted or substituted $C_{1-10}$alkyl, unsubstituted or substituted $C_{2-10}$alkenyl, unsubstituted or substituted $C_{3-10}$cycloalkyl, unsubstituted or substituted $C_{6-14}$aryl, or any two adjacent or geminal $R_1$-$R_{12}$ groups are bonded together to form, together with the atoms to which they are attached, a 5-14-membered monocyclic, polycyclic, heterocyclic, carbocyclic, saturated or unsaturated ring system and any of $R_1$-$R_{12}$, including rings formed therewith are achiral or chiral; and
$R^1$-$R^8$ are independently selected from H, $C_{1-10}$alkyl, or aryl; and
$Q^1$-$Q^8$ are independently selected from unsubstituted or substituted $C_1$-$C_{10}$alkylene and unsubstituted or substituted $C_1$-$C_{10}$alkenylene where adjacent or geminal substituents on $Q^1$-$Q^8$ are joined together to form, including the atoms to which they are attached, one or more unsubstituted or substituted 5-14-membered monocyclic, polycyclic, heterocyclic, carbocyclic, saturated, unsaturated or metallocenyl ring systems, and/or one or more of the carbon atoms in $Q^1$-$Q^8$ is optionally replaced with a heteromoiety selected from O, S, NH and N($C_{1-6}$alkyl) and any of $Q^1$-$Q^8$ is chiral or achiral.

In an embodiment of the invention, the metal catalysts may also comprise one or more of non-coordinating or coordinating, neutral or anionic and/or Lewis basic ligands, depending on the valency and size characteristics of the metal as would be known to those skilled in the art.

In an embodiment of the invention, such ligands include, but are not limited to phosphines, diphospines, cyclooctene, cyclooctadiene, halo (in particular Cl), OH, H, CO, pyridine, benzene, benzene derivatives and acetonitrile.

In an embodiment of the invention, the catalyst may also be neutral, monocationic or dicationic.

In an embodiment of the invention, the catalytic system characterizing the process of the instant invention may comprise a base. Said base can be the substrate itself, if the latter is basic, or any conventional base. One can cite, as non-limiting examples, organic non-coordinating bases such as DBU, an alkaline or alkaline-earth metal carbonate, a carboxylate salt such as sodium or potassium acetate, or an alcoholate or hydroxide salt. Preferred bases are the alcoholate or hydroxide salts selected from the group consisting of the compounds of formula $(R^9O)_2M'$ and $R^9OM''$, wherein M' is an alkaline-earth metal, M'' is an alkaline metal and $R^9$ stands for hydrogen or a linear or branched alkyl group.

A typical hydrogenation process implies the mixture of the substrate with a metal catalyst with or without a base, in the presence or absence of a solvent, and then treating such a mixture with hydrogen at a chosen pressure and temperature.

The catalyst can be added to the reaction medium in a large range of concentrations. As non-limiting examples, one can cite as complex concentration values those ranging from 0.1 ppm to 50,000 ppm, relative to the amount of substrate, thus representing respectively a substrate/complex (S/com) ratio of $10^7$ to 20. Preferably, the complex concentration will be comprised between 0.1 and 1000 ppm, i.e. a S/com ratio of $10^7$ to 1000 respectively. More preferably, there will be used concentrations in the range of 0.5 to 10,000 ppm, corresponding to a S/com ratio of 100 to $2 \times 10^6$ respectively.

If required, useful quantities of base, added to the reaction mixture, may be comprised in a relatively large range. One can cite, as non-limiting examples, ranges between 1 to 50,000 molar equivalents relative to the complex (e.g. base/com=0.5 to 50,000), or 100 to 20,000, or even between 400 and 10,000 molar equivalents. However, it should be noted that it is also possible to add a small amount of base (e.g. base/com=1 to 3) to achieve high yields.

In the processes of this invention, the hydrogenation reaction can be carried out in the presence or absence of a solvent. When a solvent is required or used for practical reasons, then any solvent can be used for the purposes of the invention. Non-limiting examples include aromatic solvents such as benzene, toluene or xylene, hydrocarbon solvents such as hexane or cyclohexane, ethers such as tetrahydrofuran, or yet primary or secondary alcohols, or mixtures thereof. A person skilled in the art is well able to select the solvent most convenient in each case to optimize the hydrogenation reaction.

The temperature at which the transfer hydrogenation can be carried out is comprised between 0° C. and 250° C., more preferably in the range of between 20° C. and 150° C. Of course, a person skilled in the art is also able to select the preferred temperature as a function of the melting and boiling point of the starting and final products.

Standard hydrogenation conditions, as used herein, typically implies the mixture of the diformate ester with a metal catalyst with or without a base, possibly in the presence or absence of a solvent, and then treating such a mixture with hydrogen gas at a chosen pressure and temperature. Varying the reaction conditions, including for example, temperature, pressure, solvent and reagent ratios, to optimize the yield of the desired product would be well within the abilities of a person skilled in the art.

(III) Examples

The disclosure will now be described in further details by way of the following examples, wherein the temperatures are indicated in degrees centigrade and the abbreviations have the usual meaning in the art. All the procedures described hereafter have been carried out under an inert atmosphere unless stated otherwise. All preparations and manipulations were carried out under $H_2$, $N_2$ or Ar atmospheres with the use of standard Schlenk, vacuum line and glove box techniques in dry, oxygen-free solvents. Deuterated solvents were degassed and dried over activated molecular sieves. NMR spectra were recorded on a 400 MHz spectrometer (400 MHz for $^1H$, 100 MHz for $^{13}C$ and 162 MHz for $^{31}P$). All $^{31}P$ chemical shifts were measured relative to 85% $H_3PO_4$ as an external reference. $^1H$ and $^{13}C$ chemical shifts were measured relative to partially deuterated solvent peaks but are reported relative to tetramethylsilane.

Example 1. Preparation of $RuCl_2(Ph_2PCH_2CH_2NH_2)_2$

A mixture of $[RuCl_2(cod)]n$ (5.6 g, 20 mmol) and $Ph_2PCH_2CH_2NH_2$ (9.2 g, 40 mmol) in toluene (250 ml) was refluxed under argon for 12 hours. The mixture was cooled to room temperature, filtered, and the yellow solids washed with toluene and dried under vacuum. Yield=10.97 g.

Example 2. Preparation of $RuCl_2(^iPr_2PCH_2CH_2NH_2)_2$

A mixture of $[RuCl_2(cod)]n$ (6.35 g, 22.6 mmol) and $^iPr_2PCH_2CH_2NH_2$ (7.30 g, 45.3 mmol) in toluene (100 ml) was refluxed under argon for 6 hours. The mixture was cooled to room temperature and hexanes (100 ml) added. The suspension was stirred for 2 hours under argon, then filtered, and the solids washed with hexanes and dried under vacuum. Yield=9.50 g.

Example 3. Preparation of $RuCl_2(^tBu_2PCH_2CH_2NH_2)_2$

A mixture of $[RuCl_2(cod)]n$ (6.87 g, 24.5 mmol) and $^tBu_2PCH_2CH_2NH_2$ (9.27 g, 49.0 mmol) in toluene (100 ml) was refluxed under argon for 6 hours. The mixture was cooled to room temperature and hexanes (100 ml) added. The suspension was stirred for 2 hours under argon, then filtered, and the solids washed with hexanes and dried under vacuum. Yield=12.05 g.

Example 4. Preparation of $[RuCl(p\text{-cymene})(Ph_2PCH_2CH_2NH_2)]Cl$

A mixture of $[RuCl_2(p\text{-cymene})]_2$ (3.06 g, 5 mmol) and $Ph_2PCH_2CH_2NH_2$ (2.29 g, 10 mmol) in toluene (25 ml) was refluxed under argon for 2 hours. The mixture was cooled to room temperature and concentrated to about 10 ml and hexanes (50 ml) added. The mixture was stirred for 2 hours, then filtered, and the yellow solids washed with hexanes and dried under vacuum. Yield=4.28 g.

Example 5. Preparation of $[RuCl(p\text{-cymene})(^iPr_2PCH_2CH_2NH_2)]Cl$

A mixture of $[RuCl_2(p\text{-cymene})]_2$ (3.06 g, 5 mmol) and $^iPr_2PCH_2CH_2NH_2$ (1.61 g, 10 mmol) in toluene (25 ml) was refluxed under argon for 2 hours. The mixture was cooled to room temperature and concentrated to about 10 ml and hexanes (50 ml) added. The mixture was stirred for 2 hours, then filtered, and the yellow solids washed with hexanes and dried under vacuum. Yield=4.02 g.

Example 6. Preparation of [RuCl(p-cymene)($^t$Bu$_2$PCH$_2$CH$_2$NH$_2$)]Cl

A mixture of [RuCl$_2$(p-cymene)]$_2$ (3.06 g, 5 mmol) and $^t$Bu$_2$PCH$_2$CH$_2$NH$_2$ (1.89 g, 10 mmol) in toluene (25 ml) was refluxed under argon for 2 hours. The mixture was cooled to room temperature and concentrated to about 10 ml and hexanes (50 ml) added. The mixture was stirred for 2 hours, then filtered, and the yellow solids washed with hexanes and dried under vacuum. Yield=4.36 g.

Example 7. Preparation of RuCl$_2$((Ph$_2$PCH$_2$CH$_2$)$_2$NH)

Toluene (10 ml) was added to a mixture of [RuCl$_2$(cod)]$_n$ (0.294 g, 1.05 mmol), triethylamine (0.212 g, 2.10 mmol) and (Ph$_2$PCH$_2$CH$_2$)$_2$NH.HCl (0.50 g, 1.05 mmol) and the mixture refluxed under argon for 20 hours. The mixture was cooled to room temperature and ether (40 ml) added. The mixture was stirred for 1 hour, then the yellow solid was filtered and washed with ether, then methanol, then ether and dried under vacuum. Yield=0.521 g.

Example 8. Preparation of RuCl$_2$(($^i$Pr$_2$PCH$_2$CH$_2$)$_2$NH)

Figure 1:
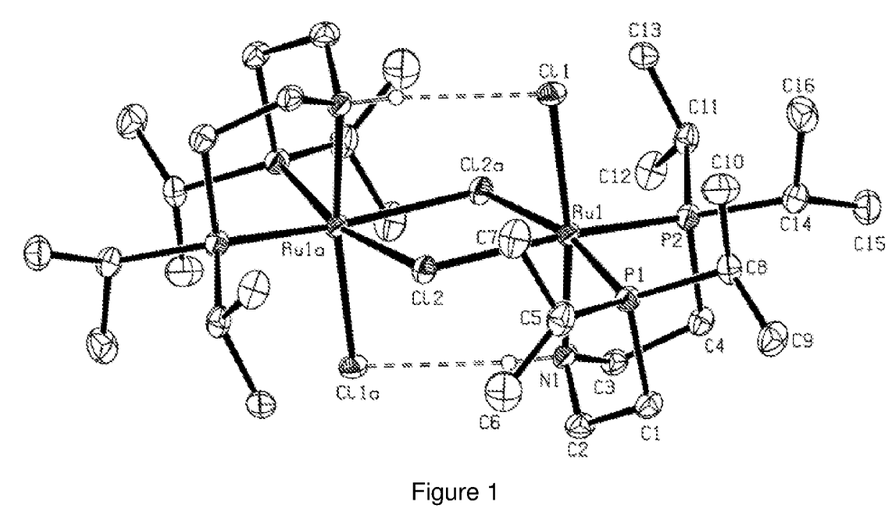
FIG. 1 shows the X-ray structure of the ruthenium complex [RuCl$_2$(($^i$Pr$_2$PCH$_2$CH$_2$)$_2$NH)]$_2$.

Toluene (10 ml) was added to a mixture of [RuCl$_2$(cod)]$_n$ (0.92 g, 3.27 mmol) and ($^i$Pr$_2$PCH$_2$CH$_2$)$_2$NH (1.0 g, 3.27 mmol) and the mixture refluxed for 4 hours. The mixture was cooled to room temperature and the yellow solid was filtered and washed with ether and dried under vacuum. Yield=1.451 g. Crystals of [RuCl$^2$(($^i$Pr$_2$PCH$_2$CH$_2$)$_2$NH)]$_2$ were prepared by layering a dichloromethane solution of the compound with diethyl ether.

Example 9. Preparation of RuH$_4$(($^i$Pr$_2$PCH$_2$CH$_2$)$_2$NH)

Figure 2:
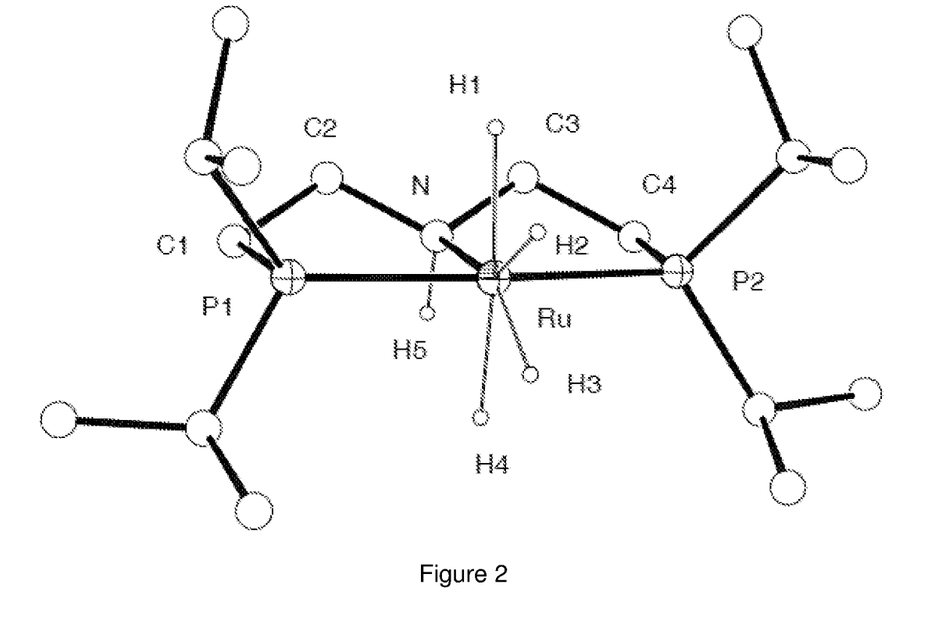
FIG. 2 shows the optimized DFT structure of RuH$_4$(($^i$Pr$_2$PCH$_2$CH$_2$)$_2$NH).
Figure 3:
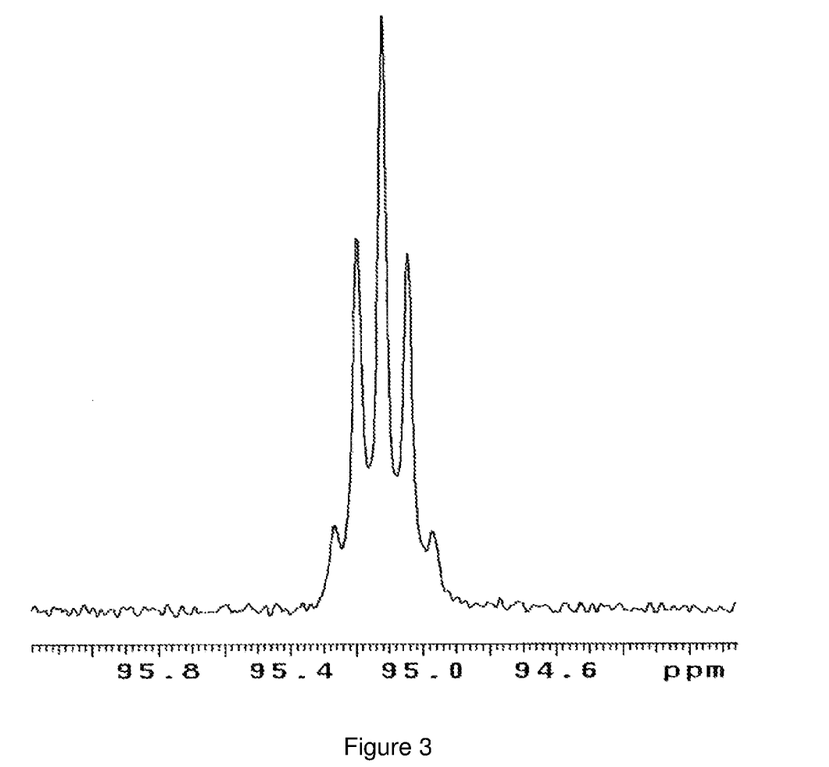
FIG. 3 shows the $^{31}$P NMR spectrum of RuH$_4$(($^i$Pr$_2$PCH$_2$CH$_2$)$_2$NH).
Figure 4:
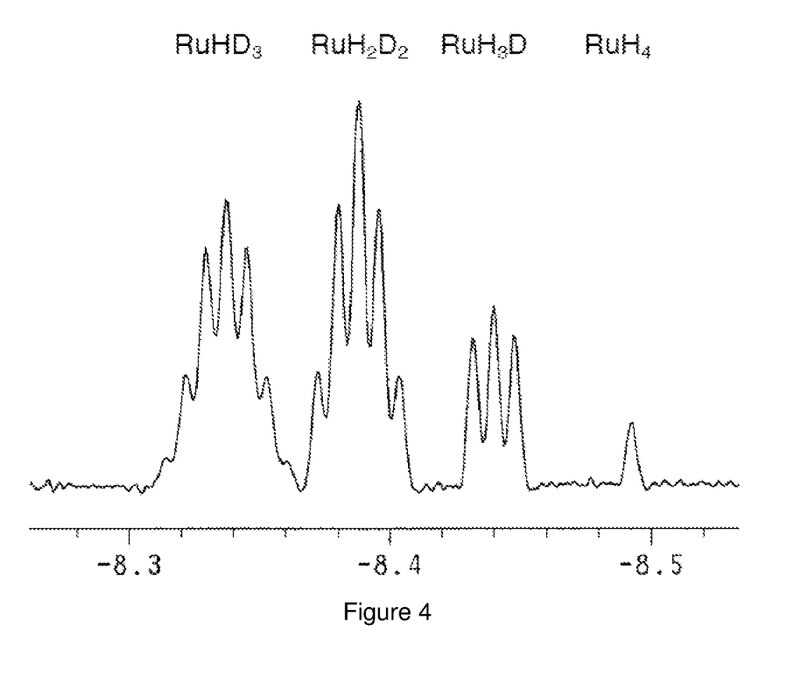
FIG. 4 shows the isotopomers in the $^1$H{$^{31}$P} NMR spectrum of partially deuterated RuH$_4$(($^i$Pr$_2$PCH$_2$CH$_2$)$_2$NH).

2-Propanol (2 ml) was added to a mixture of RuCl$_2$(($^i$Pr$_2$PCH$_2$CH$_2$)$_2$NH) (200 mg, 0.42 mmol) and KOtBu (141 mg, 1.25 mmol) and the mixture stirred for 6 hours under hydrogen gas at 60° C. The mixture was cooled to room temperature, filtered and hexanes (10 ml) added. The tan colored solid was filtered, washed with hexanes and dried under vacuum. Yield=152 mg. Deuterated isotopomers were generated by preparing a solution of RuH$_4$(($^i$Pr$_2$PCH$_2$CH$_2$)$_2$NH) in C$_6$D$_6$.

Example 10. Preparation of [RuH$_2$(($^i$Pr$_2$PCH$_2$CH$_2$)$_2$NH)]$_2$

Figure 5:
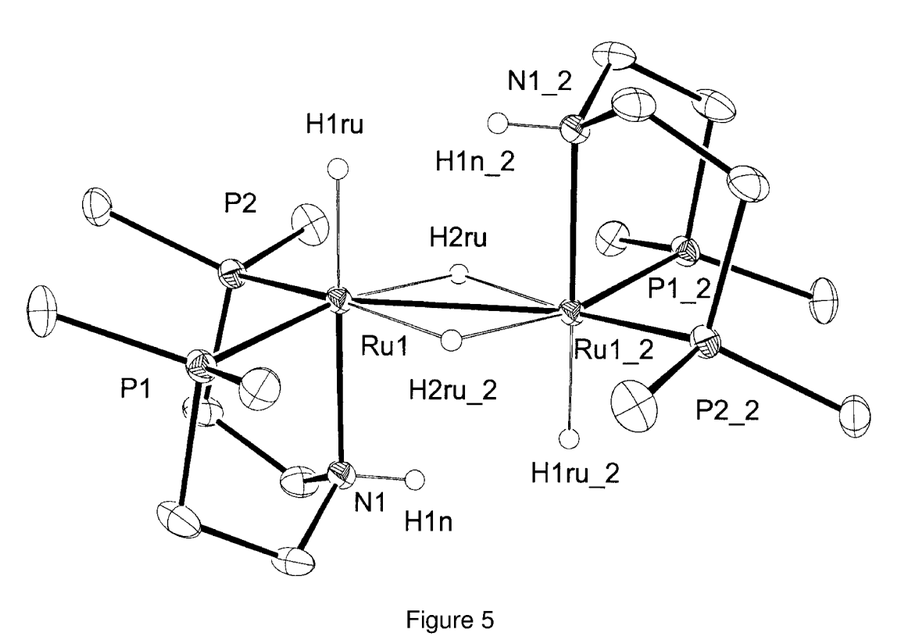
FIG. 5 shows the X-ray structure of the ruthenium complex [RuH$_2$(($^i$Pr$_2$PCH$_2$CH$_2$)$_2$NH)]$_2$ with the CH$_3$ groups removed for clarity.

Hexanes (5 ml) was added to RuH$_4$(($^i$Pr$_2$PCH$_2$CH$_2$)$_2$NH) (50 mg, 0.12 mmol) and the suspension was refluxed for 18 hours. It was slowly cooled to room temperature and the red crystals were filtered and dried under vacuum. Yield=42 mg. Crystals of [RuH$_2$(($^i$Pr$_2$PCH$_2$CH$_2$)$_2$NH)]$_2$ were prepared by refluxing a solution of the compound in hexanes then very slowly cooling to room temperature.

Example 11. Preparation of RuCl$_2$(($^t$Bu$_2$PCH$_2$CH$_2$)$_2$NH)

2-Propanol (10 ml) was added to a mixture of [RuCl$_2$(benzene)]$_2$ (250 mg, 0.50 mmol) and ($^t$Bu$_2$PCH$_2$CH$_2$)$_2$NH (362 mg, 1.00 mmol) and the mixture refluxed for 18 hours. The mixture was cooled to room temperature and the grey solid was filtered and washed with 2-propanol, then ether and dried under vacuum. Yield=320 mg.

Example 12. Preparation of RuCl$_2$((Cy$_2$PCH$_2$CH$_2$)$_2$NH)

Toluene (10 ml) was added to a mixture of [RuCl$_2$(cod)]n (0.60 g, 2.15 mmol) and (Cy$_2$PCH$_2$CH$_2$)$_2$NH (1.0 g, 2.15 mmol) and the mixture refluxed for 20 hours. The mixture was cooled to room temperature and diethyl ether (40 ml) added. The mixture was stirred for 1 hour, then filtered and the yellow solids washed with ether and dried under vacuum. Yield=1.13 g.

Example 13. Preparation of RuCl$_2$((Ad$_2$PCH$_2$CH$_2$)$_2$NH)

2-Propanol (10 ml) was added to a mixture of [RuCl$_2$(benzene)]$_2$ (250 mg, 0.50 mmol) and (Ad$_2$PCH$_2$CH$_2$)$_2$NH (675 mg, 1.00 mmol) and the mixture refluxed for 18 hours. The mixture was cooled to room temperature and the yellow solid was filtered and washed with 2-propanol, then ether and dried under vacuum. Yield=602 mg.

Example 14. Preparation of RuHCl(CO)[(Ph$_2$PCH$_2$CH$_2$)$_2$NH]

Toluene (20 ml) was added to (Ph$_2$PCH$_2$CH$_2$)$_2$NH.HCl (1.2 g, 2.5 mmol), followed by NaOH solution (10 ml, 15%) under argon and the resulting mixture stirred at room temperature until the solid dissolved. The aqueous layer was removed and the organic layer was washed with water (2×10 ml); then dried with Na$_2$SO$_4$. The aminodiphosphine solution was added to RuHCl(CO)(PPh$_3$)$_3$ (2.3 g, 2.4 mmol) and the resulting suspension refluxed for 15 hours under argon. It was cooled to room temperature and hexanes (20 ml) added. The white precipitate was filtered, washed with hexanes and dried under vacuum. Yield=1.38 g.

Example 15. Preparation of RuHCl(CO)[($^i$Pr$_2$PCH$_2$CH$_2$)$_2$NH]

A mixture of RuHCl(CO)(PPh$_3$)$_3$ (31.2 g, 32.7 mmol) and ($^i$Pr$_2$PCH$_2$CH$_2$)$_2$NH (10.0 g, 32.7 mmol) in toluene (50 ml) was refluxed for 15 hours under argon. The reaction mixture was cooled to room temperature and hexanes (250 ml) was added to precipitate the product. It was filtered, washed with hexanes and dried under vacuum. Yield=9.52 g.

Example 16. Preparation of RuHCl(CO)[($^t$Bu$_2$PCH$_2$CH$_2$)$_2$N$_{11}$]

A mixture of RuHCl(CO)(PPh$_3$)$_3$ (26.3 g, 27.7 mmol) and ($^t$Bu$_2$PCH$_2$CH$_2$)$_2$NH (10.0 g, 27.7 mmol) in toluene (50 ml) was refluxed for 15 hours under argon. The reaction mixture was cooled to room temperature and hexanes (250 ml) was added to precipitate the product. It was filtered, washed with hexanes and dried under vacuum. Yield=13.93 g.

Example 17. Preparation of RuHCl(CO)[(Cy$_2$PCH$_2$CH$_2$)$_2$N$_{11}$]

A mixture of RuHCl(CO)(PPh$_3$)$_3$ (20.7 g, 21.7 mmol) and (Cy$_2$PCH$_2$CH$_2$)$_2$NH (10.6 g, 22.8 mmol) in toluene (50 ml) was refluxed for 20 hours under argon. The reaction mixture was cooled to about 60° C. and filtered while hot. The white solids were washed with toluene, then ether and dried under vacuum. Yield=10.1 g.

Example 18. Preparation of RuHCl(CO) [(Ad$_2$PCH$_2$CH$_2$)$_2$N$_{11}$]

A mixture of RuHCl(CO)(PPh$_3$)$_3$ (2.82 g, 2.96 mmol) and (Cy$_2$PCH$_2$CH$_2$)$_2$NH (2.0 g, 2.96 mmol) in toluene (10 ml) was refluxed for 20 hours under argon. The reaction mixture was cooled to room temperature and ether (10 ml) added. The white solids were washed with toluene, then ether and dried under vacuum. Yield=2.23 g.

Example 19. Preparation of IrHCl$_2$(($^i$Pr$_2$PCH$_2$CH$_2$)$_2$NH)

Ammonium chloride (0.175 g, 3.27 mmol) and [Ir(coe)$_2$Cl]$_2$ (1.47 g, 1.64 mmol) were added to a solution of ($^i$Pr$_2$PCH$_2$CH$_2$)$_2$NH (1.0 g, 3.27 mmol) in THF (10 ml) and the mixture stirred for 20 hours at 65° C. It was cooled to room temperature and ether (30 ml) added. The colorless product was filtered, washed with ether and dried under vacuum. Yield=1.36 g.

Example 20. Preparation of IrHCl$_2$(($^t$Bu$_2$PCH$_2$CH$_2$)$_2$ NH)

Trimethylammonium chloride (0.264 g, 2.77 mmol) and [Ir(coe)$_2$Cl]$_2$ (1.24 g, 1.38 mmol) were added to a solution of ($^t$Bu$_2$PCH$_2$CH$_2$)$_2$NH (1.0 g, 2.77 mmol) in THF (10 ml) and the mixture stirred for 24 hours at 65° C. under argon. It was cooled to room temperature and ether (40 ml) added. The colorless product was filtered, washed with ether and dried under vacuum. Yield=1.55 g.

Example 21. Preparation of IrH$_2$Cl ((Cy$_2$PCH$_2$CH$_2$)$_2$NH)

2-Propanol (10 ml) was added to a mixture of [IrCl(coe)$_2$]$_2$ (0.95 g, 1.06 mmol) and (Cy$_2$PCH$_2$CH$_2$)$_2$NH (1.0 g, 2.15 mmol) and the resulting suspension was stirred for 2 hours at 80° C. under argon. It was then cooled to room temperature and hexanes (20 ml) added. The mixture was stirred for 1 hour, then filtered, the solids washed with ether and dried under vacuum. Yield=0.893 g.

Example 22. Preparation of FeCl$_2$(($^i$Pr$_2$PCH$_2$CH$_2$)$_2$ NH)

THF (10 ml) was added to a mixture of FeCl$_2$ (0.206 g, 1.6 mmol) and ($^i$Pr$_2$PCH$_2$CH$_2$)$_2$NH (0.50 g, 1.6 mmol) and the suspension heated at reflux for 2 hours under argon. It was cooled to room temperature and ether (20 ml) added under argon. The mixture was stirred for 1 hour, then filtered, washed with ether and dried under vacuum. Yield=0.609 g.

Example 23. Preparation of FeCl$_2$(($^t$Bu$_2$PCH$_2$CH$_2$)$_2$ NH)

THF (10 ml) was added to a mixture of FeCl$_2$ (0.175 g, 1.38 mmol) and ($^t$Bu$_2$PCH$_2$CH$_2$)$_2$NH (0.50 g, 1.38 mmol) and the suspension heated at 60° C. for 20 hours under argon. It was cooled to room temperature and ether (20 ml) added under argon. The mixture was stirred for 1 hour, then filtered, washed with ether and dried under vacuum. Yield=0.640 g.

Example 24. Preparation of FeCl$_2$((Cy$_2$PCH$_2$CH$_2$)$_2$ NH)

THF (10 ml) was added to a mixture of FeCl$_2$ (0.136 g, 1.07 mmol) and (Cy$_2$PCH$_2$CH$_2$)$_2$NH (0.50 g, 1.07 mmol) and the suspension heated at 60° C. for 15 hours under argon. It was cooled to room temperature and ether (20 ml) added under argon. The mixture was stirred for 1 hour, then filtered, washed with ether and dried under vacuum. Yield=0.534 g.

Example 25. Preparation of RuCl$_2$ ((Ph$_2$PCH$_2$CH$_2$NHCH$_2$)$_2$)

Toluene (10 ml) and 2-propanol (1 ml) were added to a mixture of RuCl$_2$(PPh$_3$)$_3$ (0.99 g, 1.03 mmol) and (Ph$_2$PCH$_2$CH$_2$NHCH$_2$)$_2$ (0.5 g, 1.03 mmol) and the mixture stirred under argon at 60° C. for 4 hours. It was cooled to room temperature and stirred for 2 hours. It was then filtered under argon and the filtrate evaporated to dryness. Ether (20 ml) was added and the suspension stirred for 2 hours under argon. It was filtered, washed with ether and dried under vacuum. Yield=0.594 g.

Example 26. Preparation of RuCl$_2$ (($^i$Pr$_2$PCH$_2$CH$_2$NHCH$_2$)$_2$)

Toluene (10 ml) and 2-propanol (1 ml) were added to a mixture of RuCl$_2$(PPh$_3$)$_3$ (1.37 g, 1.43 mmol) and ($^i$Pr$_2$PCH$_2$CH$_2$NHCH$_2$)$_2$ (0.5 g, 1.43 mmol) and the mixture stirred under argon at 60° C. for 4 hours. It was cooled to room temperature and stirred for 3 hours. It was then filtered under argon and the filtrate evaporated to dryness. Ether (30 ml) was added and the suspension stirred for 2 hours under argon. It was filtered, washed with ether and dried under vacuum. Yield=0.384 g.

Example 27. Preparation of OsCl$_2$(($^i$Pr$_2$PCH$_2$CH$_2$)$_2$ NH)

Toluene (10 ml) was added to a mixture of OsCl$_2$(PPh$_3$)$_3$ (0.50 g, 0.48 mmol) and ($^i$Pr$_2$PCH$_2$CH$_2$)$_2$NH (0.146 g, 0.48 mmol) and the mixture heated at 60° C. for 1 hour under argon. It was cooled to room temperature and the solvent removed under reduced pressure. Ether (20 ml) was added under argon and the mixture was stirred for 30 minutes, then filtered, washed with ether and dried under vacuum. Yield=0.258 g.

Example 28. Preparation of Ph$_2$P(CH$_2$)$_2$NHCH$_2$Py

A solution of 2-pyridinecarboxaldehyde (2.32 g, 21.6 mmol) in THF (2.5 ml) was added to a solution of 2-(diphenylphosphino)ethylamine (4.95 gram, 21.6 mmol) in THF (5 ml) and the mixture was stirred for 3 hours at room temperature. Hexanes (10 ml) was added and the mixture placed in the freezer overnight. The imine precipitated as a white solid and this was filtered, washed with hexanes and dried under vacuum. Yield=6.2 g. This was suspended in methanol (10 ml) and sodium borohydride was added slowly in small portions. The mixture was then stirred for 2 hours then evaporated to dryness. The residue was extracted with toluene and the solution filtered through a plug of silica gel. The toluene was then evaporated to give the product as a pale yellow oil, which crystallized after 4 days at room temperature. Yield=5.4 g.

Example 29. Preparation of RuCl$_2$(PPh$_3$)(Ph$_2$P(CH$_2$)$_2$NHCH$_2$Py)

Toluene (20 ml) was added to a mixture of RuCl$_2$(PPh$_3$)$_3$ (4.2 g, 4.4 mmol) and Ph$_2$P(CH$_2$)$_2$NHCH$_2$Py (1.4 g, 4.4 mmol) and the resulting yellow suspension was stirred for 12 hours at room temperature under argon. The yellow solids were filtered, washed with ether and dried under vacuum. Yield=2.8 g.

Example 30. Hydrogenation of Ethylene Glycol Diformate Ester

Example 30.1. Hydrogenation of Ethylene Glycol Diformate Ester Using RuCl$_2$[($^i$Pr$_2$PCH$_2$CH$_2$)$_2$NH] as Catalyst The catalyst (50 mg) was added to a mixture of ethylene glycol diformate ester (4.0 g) and KOtBu (100 mg) in a 100 ml Parr pressure reactor. The mixture was degassed with hydrogen and the pressure was set to 500 psi. The mixture was stirred for 20 hours at 70° C. The NMR spectra of the reaction mixture showed 100% conversion of the ester to a mixture of ethylene glycol and methanol.

Example 30.2. Hydrogenation of Ethylene Glycol Diformate Ester Using RuHCl(CO)[($^i$Pr$_2$PCH$_2$CH$_2$)$_2$NH] as Catalyst The catalyst (50 mg) was added to a mixture of ethylene glycol diformate ester (4.0 g) and KOtBu (100 mg) in a 100 ml Parr pressure reactor. The mixture was degassed with hydrogen and the pressure was set to 500 psi. The mixture was stirred for 20 hours at 70° C. The NMR spectra of the reaction mixture showed 100% conversion of the ester to a mixture of ethylene glycol and methanol.

Example 30.3. Hydrogenation of Ethylene Glycol Diformate Ester Using IrHCl$_2$[($^i$Pr$_2$PCH$_2$CH$_2$)$_2$NH] as Catalyst The catalyst (50 mg) was added to a mixture of ethylene glycol diformate ester (4.0 g) and KOtBu (100 mg) in a 100 ml Parr pressure reactor. The mixture was degassed with hydrogen and the pressure was set to 500 psi. The mixture was stirred for 20 hours at 70° C. The NMR spectra of the reaction mixture showed 84% conversion of the ester to a mixture of ethylene glycol and methanol.

Example 30.4. Hydrogenation of Ethylene Glycol Diformate Ester Using RuHCl(CO)[(Ph$_2$PCH$_2$CH$_2$)$_2$NH] as Catalyst The catalyst (50 mg) was added to a mixture of ethylene glycol diformate ester (4.0 g) and KOtBu (100 mg) in a 100 ml Parr pressure reactor. The mixture was degassed with hydrogen and the pressure was set to 500 psi. The mixture was stirred for 20 hours at 80° C. The NMR spectra of the reaction mixture showed 100% conversion of the ester to a mixture of ethylene glycol and methanol.

Example 30.5. Deuteration of Ethylene Glycol Diformate Ester Using RuCl$_2$[($^i$Pr$_2$PCH$_2$CH$_2$)$_2$NH] as Catalyst The catalyst (50 mg) was added to a mixture of ethylene glycol diformate ester (4.0 g) and KOtBu (100 mg) in a 100 ml Parr pressure reactor. The mixture was degassed with deuterium and the pressure was set to 500 psi. The mixture was stirred for 20 hours at 70° C. The NMR spectra of the reaction mixture showed 100% conversion of the ester to a mixture of ethylene glycol and methanol isotopomers.

Example 31. Hydrogenation of Diethylene Glycol Diformate Ester

Example 31.1. Hydrogenation of Diethylene Glycol Diformate Ester Using RuCl$_2$[($^i$Pr$_2$PCH$_2$CH$_2$)$_2$NH] as Catalyst The catalyst (50 mg) was added to a mixture of diethylene glycol diformate ester (4.0 g) and KOtBu (100 mg) in a 100 ml Parr pressure reactor. The mixture was degassed with hydrogen and the pressure was set to 500 psi. The mixture was stirred for 20 hours at 80° C. The NMR spectra of the reaction mixture showed 100% conversion of the ester to a mixture of diethylene glycol and methanol.

Example 31.2. Hydrogenation of Diethylene Glycol Diformate Ester Using RuHCl(CO)[($^i$Pr$_2$PCH$_2$CH$_2$)$_2$NH] as Catalyst

The catalyst (50 mg) was added to a mixture of diethylene glycol diformate ester (4.0 g) and KOtBu (100 mg) in a 100 ml Parr pressure reactor. The mixture was degassed with hydrogen and the pressure was set to 500 psi. The mixture was stirred for 20 hours at 80° C. The NMR spectra of the reaction mixture showed 100% conversion of the ester to a mixture of diethylene glycol and methanol.

Example 31.3. Hydrogenation of Diethylene Glycol Diformate Ester Using RuHCl(CO)[(Ph$_2$PCH$_2$CH$_2$)$_2$NH] as Catalyst The catalyst (50 mg) was added to a mixture of diethylene glycol diformate ester (4.0 g) and KOtBu (100 mg) in a 100 ml Parr pressure reactor. The mixture was degassed with hydrogen and the pressure was set to 500 psi. The mixture was stirred for 20 hours at 80° C. The NMR spectra of the reaction mixture showed 100% conversion of the ester to a mixture of diethylene glycol and methanol.

Example 33. Hydrogenation of 1,4-Benzenedimethanol Diformate Ester

Example 33.1. Hydrogenation of 1,4-benzenedimethanol diformate ester Using RuCl$_2$[($^i$Pr$_2$PCH$_2$CH$_2$)$_2$NH] as Catalyst The catalyst (50 mg) was added to a mixture of diethylene glycol diformate ester (2.0 g) and KOtBu (100 mg) in a 100 ml Parr pressure reactor and 2.0 ml of methanol added to dissolve the ester. The mixture was degassed with hydrogen and the pressure was set to 500 psi. The mixture was stirred for 15 minutes at room temperature. The NMR spectra of the reaction mixture showed 100% conversion of the ester to a mixture of 1,4-benzenedimethanol and methanol.

Example 33.2. Hydrogenation of 1,4-benzenedimethanol diformate ester Using RuHCl(CO)[($^i$Pr$_2$PCH$_2$CH$_2$)$_2$NH] as Catalyst The catalyst (50 mg) was added to a mixture of diethylene glycol diformate ester (2.0 g) and KOtBu (100 mg) in a 100 ml Parr pressure reactor and 2.0 ml of methanol added to dissolve the ester. The mixture was degassed with hydrogen and the pressure was set to 500 psi. The mixture was stirred for 15 minutes at room temperature. The NMR spectra of the reaction mixture showed 100% conversion of the ester to a mixture of 1,4-benzenedimethanol and methanol.

Example 34. Preparation of Sodium Formate from Carbon Dioxide and Hydrogen

Example 34.1. Preparation of Sodium Formate Using RuCl$_2$[($^i$Pr$_2$PCH$_2$CH$_2$)$_2$NH] as Catalyst Water (10.0 g) was added to a mixture of sodium hydroxide (1.4 g) and the catalyst (10 mg) in a 100 ml Parr pressure reactor. The mixture was degassed with a 1:1 mixture of carbon dioxide and hydrogen and the pressure was set to 500 psi. The mixture was stirred for 4 hours at 130° C. It was then cooled to room temperature and the residue evaporated to dryness. The NMR spectra of the solid showed that it is composed of 29.5% sodium formate and 70.5% sodium bicarbonate.

Example 34.2. Preparation of Sodium Formate Using RuCl$_2$[($^i$Pr$_2$PCH$_2$CH$_2$)$_2$NH] as Catalyst Water (10.0 g) was added to a mixture of sodium hydroxide (1.65 g) and the catalyst (10 mg) in a 100 ml Parr pressure reactor. The mixture was degassed with a 1:1 mixture of carbon dioxide and hydrogen and the pressure was set to 500 psi. The mixture was stirred for 4 hours at 140° C. It was then cooled to room temperature and the residue evaporated to dryness. The NMR spectra of the solid showed that it is composed of 71% sodium formate and 29% sodium bicarbonate.

Example 34.3. Preparation of Sodium Formate Using RuCl$_2$[($^i$Pr$_2$PCH$_2$CH$_2$)$_2$NH] as Catalyst Water (10.0 g) was added to a mixture of sodium hydroxide (1.65 g) and the catalyst (10 mg) in a 100 ml Parr pressure reactor. The mixture was degassed with a 1:1 mixture of carbon dioxide and hydrogen and the pressure was set to 500 psi. The mixture was stirred for 4 hours at 150° C. It was then cooled to room temperature and the residue evaporated to dryness. The NMR spectra of the solid showed that it is composed of 82% sodium formate and 18% sodium bicarbonate.

Example 35. Preparation of Sodium Formate from Sodium Bicarbonate and Hydrogen

Example 35.1. Preparation of Sodium Formate Using RuCl$_2$[($^i$Pr$_2$PCH$_2$CH$_2$)$_2$NH] as Catalyst Water (10.0 g) was added to a mixture of sodium bicarbonate (2.5 g) and the catalyst (10 mg) in a 100 ml Parr pressure reactor. The mixture was degassed with hydrogen and the pressure was set to 500 psi. The mixture was stirred for 18 hours at 150° C. It was then cooled to room temperature and the residue evaporated to dryness. The NMR spectra of the solid showed that it is composed of 84% sodium formate and 16% sodium bicarbonate.

Example 35.2. Preparation of Sodium Formate Using RuCl$_2$[($^i$Pr$_2$PCH$_2$CH$_2$)$_2$NH] as Catalyst Water (10.0 g) was added to a mixture of sodium bicarbonate (2.91 g) and the catalyst (10 mg) in a 100 ml Parr pressure reactor. The mixture was degassed with hydrogen and the pressure was set to 500 psi. The mixture was stirred for 6 hours at 150° C. It was then cooled to room temperature and the residue evaporated to dryness. The NMR spectra of the solid showed that it is composed of 80% sodium formate and 20% sodium bicarbonate.

Example 36. Conversion of RuCl$_2$[($^i$Pr$_2$PCH$_2$CH$_2$)$_2$NH] to RuHCl(CO)[($^i$Pr$_2$PCH$_2$CH$_2$)$_2$NH] During Carbon Dioxide Hydrogenation Water (10.0 g) was added to a mixture of sodium hydroxide (1.4 g) and RuCl$_2$[($^i$Pr$_2$P(CH$_2$)$_2$)$_2$NH] (50 mg) in a 100 ml Parr pressure reactor. The mixture was degassed with a 1:1 mixture of carbon dioxide and hydrogen and the pressure was set to 500 psi. The mixture was stirred for 4 hours at 70° C. It was then cooled to room temperature and the mixture filtered. The residue was washed with water, then ether and dried under vacuum. The NMR spectra of the solid showed that it is RuHCl(CO)[($^i$Pr$_2$PCH$_2$CH$_2$)$_2$NH]. Yield=27 mg.

We claim:
1. A process for the hydrogenation of diformate esters of Formula (I):

(I)

wherein, Y represents an unsubstituted or substituted alkylene, an unsubstituted or substituted alkenylene, or an unsubstituted or substituted arylene, and one or more of the carbon atoms in Y is optionally replaced with a heteromoiety selected from the group consisting of O, S, NH and N($C_{1-6}$alkyl) and Y is chiral or achiral, where adjacent or geminal substituents on Y may be joined together to form, including the atoms to which they are attached, one or more unsubstituted or substituted monocyclic, polycyclic, heterocyclic, carbocyclic, saturated, unsaturated or metallocenyl ring systems, wherein the compound of Formula (I) is contacted with a metal catalyst in the presence of hydrogen gas to provide compounds of Formula (II) and methanol (Formula (III)):

(II)

(III)

wherein the metal catalyst comprises compounds of chromium (Cr), manganese (Mn), iron (Fe), cobalt (Co), nickel (Ni), copper (Cu), molybdenum (Mo), ruthenium (Ru), rhodium (Rh), palladium (Pd), tungsten (W), rhenium (Re), osmium (Os), iridium (Ir) or platinum (Pt);

and wherein the catalyst comprises at least one ligand that bonds to the metal via a nitrogen atom, wherein the nitrogen-coordinating ligand is selected from the group consisting of one or more of a PN, PNP, PNNP and PNN ligand wherein, PN is a bidentate ligand of the formula $R_1R_2P-Q^1-NR^1R^2$;

PNP is a tridentate ligand of the formula $R_3R_4P-Q^2-NR^3-Q^3-PR_5R_6$;

PNNP is a tetradentate ligand of the formula $R_7R_8P-Q^4-NR^4-Q^5-NR^5-Q^6-PR_9R_{10}$;

PNN is a tridentate ligand of the formula $R_{11}R_{12}P-Q^7-NR^6-Q^8-NR^7R^8$;

wherein $R_1$-$R_{12}$ are independently selected from the group consisting of H, unsubstituted or substituted $C_{1-10}$alkyl, unsubstituted or substituted $C_{2-10}$alkenyl, unsubstituted or substituted $C_{3-10}$cycloalkyl, unsubstituted or substituted $C_{6-14}$aryl, or any two adjacent or geminal $R_1$-$R_{12}$ groups are bonded together to form, together with the atoms to which they are attached, a 5-14-membered monocyclic, polycyclic, heterocyclic, carbocyclic, saturated or unsaturated ring system and any of $R_1$-$R_{12}$, including rings formed therewith are achiral or chiral;

$Q^1$-$Q^8$ are independently selected from the group consisting of unsubstituted or substituted $C_1$-$C_{10}$alkylene and unsubstituted or substituted $C_1$-$C_{10}$alkenylene, and/or one or more of the carbon atoms in $Q^1$-$Q^8$ is optionally replaced with a heteromoiety selected from the group consisting of O, S, NH and N($C_{1-6}$alkyl) and any of $Q^1$-$Q^8$ is chiral or achiral; or adjacent or geminal substituents on $Q^1$-$Q^8$ are joined together to form, including the atoms to which they are attached, one or more unsubstituted or substituted 5-14-membered monocyclic, polycyclic, heterocyclic, carbocyclic, saturated, unsaturated or metallocenyl ring systems.

2. A process according to claim 1, wherein the diformate esters of Formula (I) are derived from formic acid, formate salts, or mixtures thereof.

3. A process according to claim 1, wherein the diformate esters of Formula (I) are derived from ethylene glycol, propylene glycol, 1,3-propanediol, diethylene glycol and benzenedimethanol.

4. A process according to claim 1, wherein the diol hydrogenation products of Formula (II) are recovered and re-used for the preparation of diformate esters of Formula (I).

5. A process according to claim 1, wherein the metal catalyst comprises compounds of Mn, Fe, Ru, Os, Co, Rh, Re or Ir.

6. A process according to claim 1, wherein the metal catalyst further comprise one or more of non-coordinating or coordinating, neutral, anionic or Lewis basic ligands.

7. A process according to claim 6, wherein the non-coordinating, coordinating, neutral, anionic and/or Lewis basic ligands comprise phosphines, diphosphines, cyclooctene, cyclooctadiene, halo, OH, H, CO, pyridine, benzene, benzene derivatives and acetonitrile.

8. A process according to claim 7, wherein the halo is Cl.

9. A process according to claim 1, wherein the catalyst is neutral, monocationic or dicationic.

10. A process according to claim 1, further comprises contacting the compound of Formula (I) with a base.

11. A process according to claim 10, wherein the base organic non-coordinating bases, an alkaline or alkaline-earth metal carbonate, a carboxylate salt, or an alcoholate or hydroxide salt.

12. A process according to claim 11, wherein the non-coordinating base is 1,8-Diazabicycloundec-7-ene (DBU).

13. The process according to claim 11, wherein the carboxylate salt is sodium or potassium acetate.

14. A process according to claim 1, wherein the hydrogenation reaction is carried out in the presence or absence of a solvent.

* * * * *